(12) United States Patent  (10) Patent No.: US 7,945,332 B2
Schechter  (45) Date of Patent: May 17, 2011

(54) APPARATUS FOR ATTACHMENT AND REINFORCEMENT OF TISSUE, APPARATUS FOR REINFORCEMENT OF TISSUE, METHODS OF ATTACHING AND REINFORCING TISSUE, AND METHODS OF REINFORCING TISSUE

(75) Inventor: David A. Schechter, Longmont, CO (US)

(73) Assignee: VitruMed, Inc., Boulder, CO (US)

( * ) Notice: Subject to any disclaimer, the term of this patent is extended or adjusted under 35 U.S.C. 154(b) by 542 days.

(21) Appl. No.: 12/123,808

(22) Filed: May 20, 2008

(65) Prior Publication Data

US 2008/0294222 A1   Nov. 27, 2008

Related U.S. Application Data

(60) Provisional application No. 60/939,602, filed on May 22, 2007.

(51) Int. Cl.
*A61N 1/00* (2006.01)
(52) U.S. Cl. .............. 607/50; 606/51; 606/32
(58) Field of Classification Search .............. 607/1, 2, 607/3, 50; 606/32, 51
See application file for complete search history.

(56) References Cited

U.S. PATENT DOCUMENTS

| | | |
|---|---|---|
| 2,031,682 A | 2/1936 | Wappler et al. |
| 4,043,342 A | 8/1977 | Morrison, Jr. |
| 5,151,102 A | 9/1992 | Kamiyama et al. |
| 5,403,312 A | 4/1995 | Yates et al. |
| 5,688,270 A | 11/1997 | Yates et al. |
| 6,024,741 A | 2/2000 | Williamson, IV et al. |
| 6,086,586 A | 7/2000 | Hooven |
| 6,562,037 B2 | 5/2003 | Paton et al. |
| 6,626,901 B1 | 9/2003 | Treat et al. |
| 6,652,521 B2 | 11/2003 | Schulze |
| 6,682,527 B2 | 1/2004 | Strul |
| 6,726,686 B2 | 4/2004 | Buysse et al. |
| 6,743,229 B2 | 6/2004 | Buysse et al. |
| 7,025,764 B2 | 4/2006 | Paton et al. |
| 7,087,054 B2 | 8/2006 | Truckai et al. |

(Continued)

FOREIGN PATENT DOCUMENTS

JP     2004-209041 A     7/2004

OTHER PUBLICATIONS

Santini, Mario, et al., "Use of an Electrothermal Bipolar Tissue Sealing System in Lung Surgery", European Journal of Cardio-Thoracic Surgery, vol. 29, pp. 226-230, 2006.

(Continued)

*Primary Examiner* — Scott M Getzow
(74) *Attorney, Agent, or Firm* — Holland & Hart, LLP

(57) ABSTRACT

There are disclosed methods and apparatus for attachment and reinforcement of tissue, and methods and apparatus for reinforcement of tissue. In an embodiment, the apparatus includes an energy applicator configured to apply energy to generate heat within a target tissue to evaporate water to create dried tissue, and denature at least one of collagen and elastin to attach portions together, and a biopolymer applicator configured for to receive the heat generated to allow biopolymer material to change from solid to molten, and to allow the biopolymer to fill dried tissue to reinforce portions of the target tissue and provide a hermetic seal.

In another embodiment, the method includes applying energy to tissue surfaces with an energy applicator, and applying a biopolymer material into the tissue surfaces with a biopolymer applicator disposed on a housing in connection with the energy applicator. Other embodiments are also disclosed.

52 Claims, 16 Drawing Sheets

U.S. PATENT DOCUMENTS 7,090,673 B2  8/2006  Dycus et al.
7,241,296 B2  7/2007  Buysse et al.

OTHER PUBLICATIONS

Shigemura, Norihisa, et al., "A New Tissue-Sealing Technique Using the LigaSure System for Nonanatomical Pulmonary Resection: Preliminary Results of Sutureless and Stapleless Thoracoscopic Surgery", New Technology, vol. 77, pp. 1415-1419, 2004.

Tirabassi, Michael, V., et al., "Quantitation of Lung Sealing in the Survival Swing Model", Journal of Pediatric Surgery, vol. 39, No. 3, pp. 387-390, Mar. 2004.

Albanese, Craig T., et al., "Experience with 144 Consecutive Pediatric Thoracoscopic Lobectomies", Journal of Laparoendoscopic & Advanced Surgical Techniques, vol. 17, No. 3, pp. 339-341, 2007.

Cano, Indalecio, et al., "Video-Assisted Thoracoscopic Lobectomy in Infants", European Journal of Cardio-Thoracic Surgery, vol. 29, pp. 997-1000, 2006.

Shigemura, Norihisa, et al., "New Operative Method for a Giant Bulla: Sutureless and Stapleless Thoracoscopic Surgery Using the Ligasure System", European Journal of Cardio-Thoracic Surgery, vol. 22, pp. 646-648, 2002.

IPER dated Dec. 3, 2009 for application No. PCT/US2008/064248, 6 pages.

ISR dated Oct. 27, 2008 for application No. PCT/US2008/064248, 3 pages.

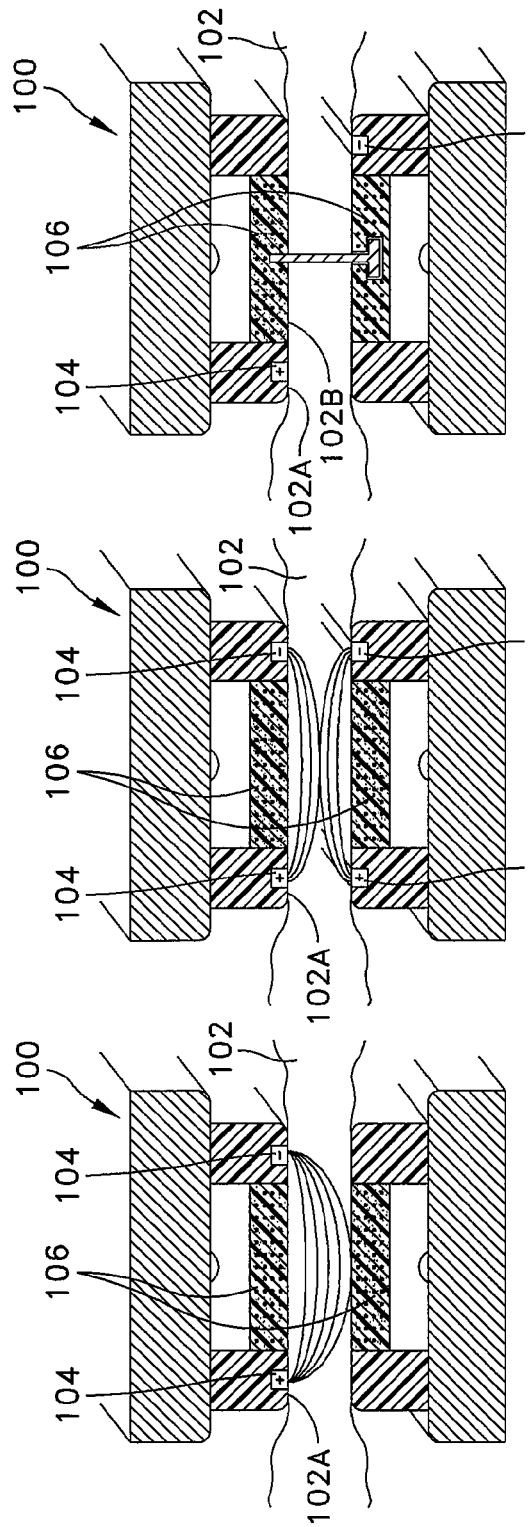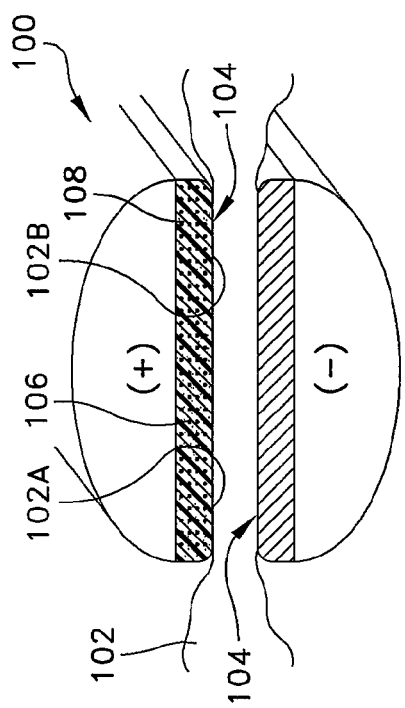
FIGURE 3
FIGURE 4
FIGURE 5
FIGURE 6

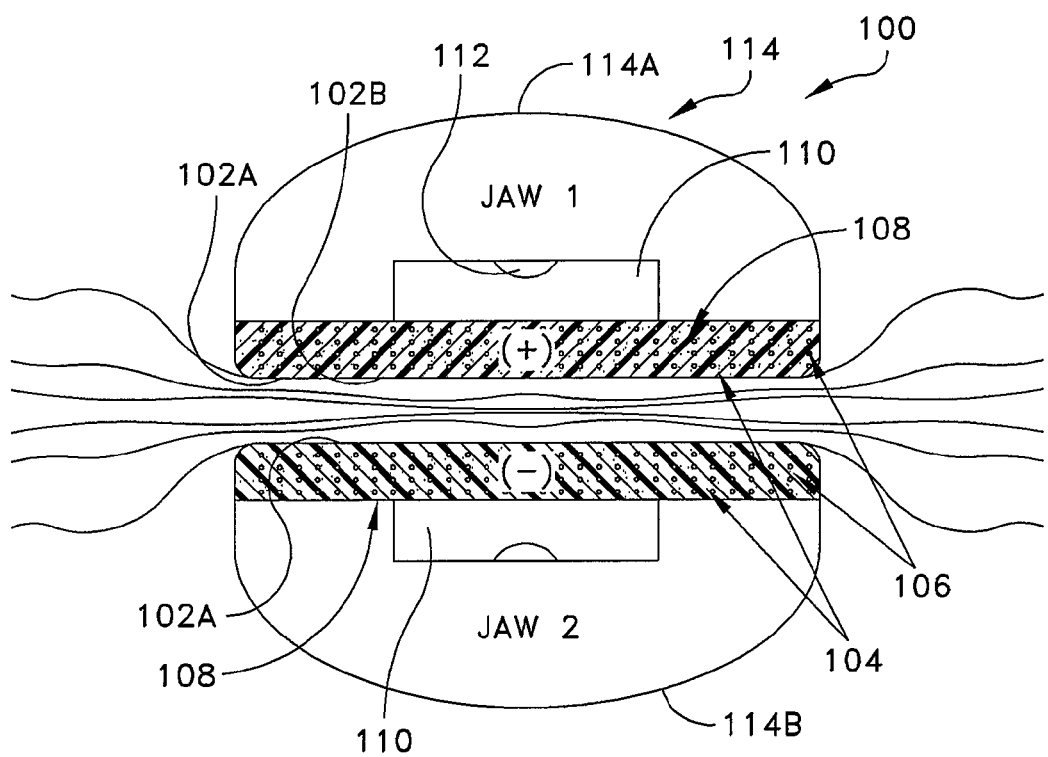
FIGURE 7
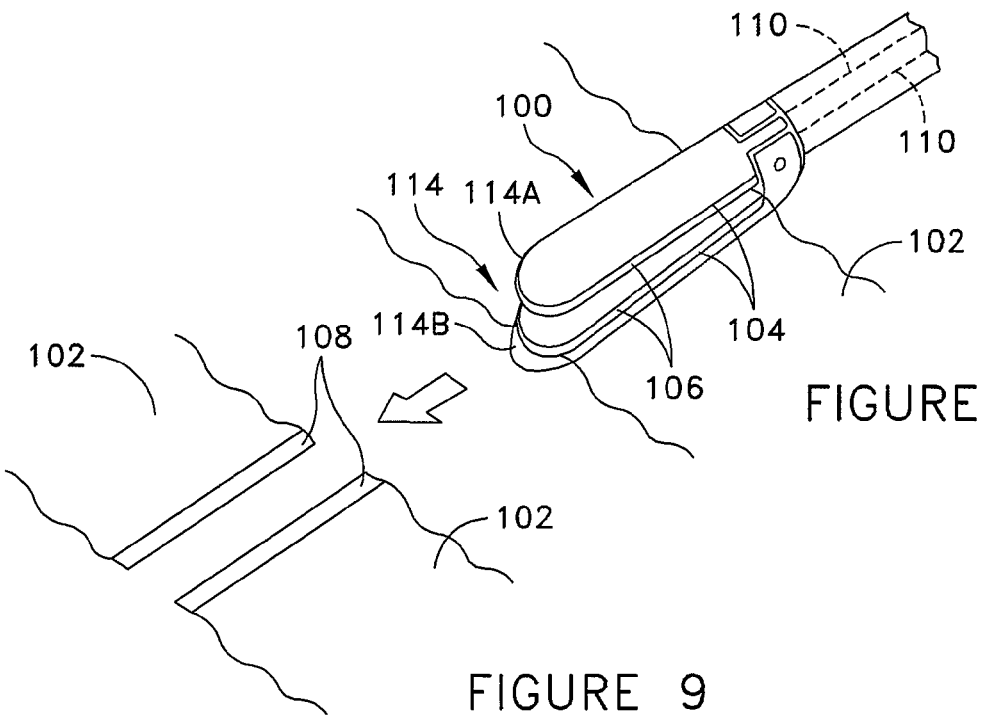
FIGURE 8
FIGURE 9

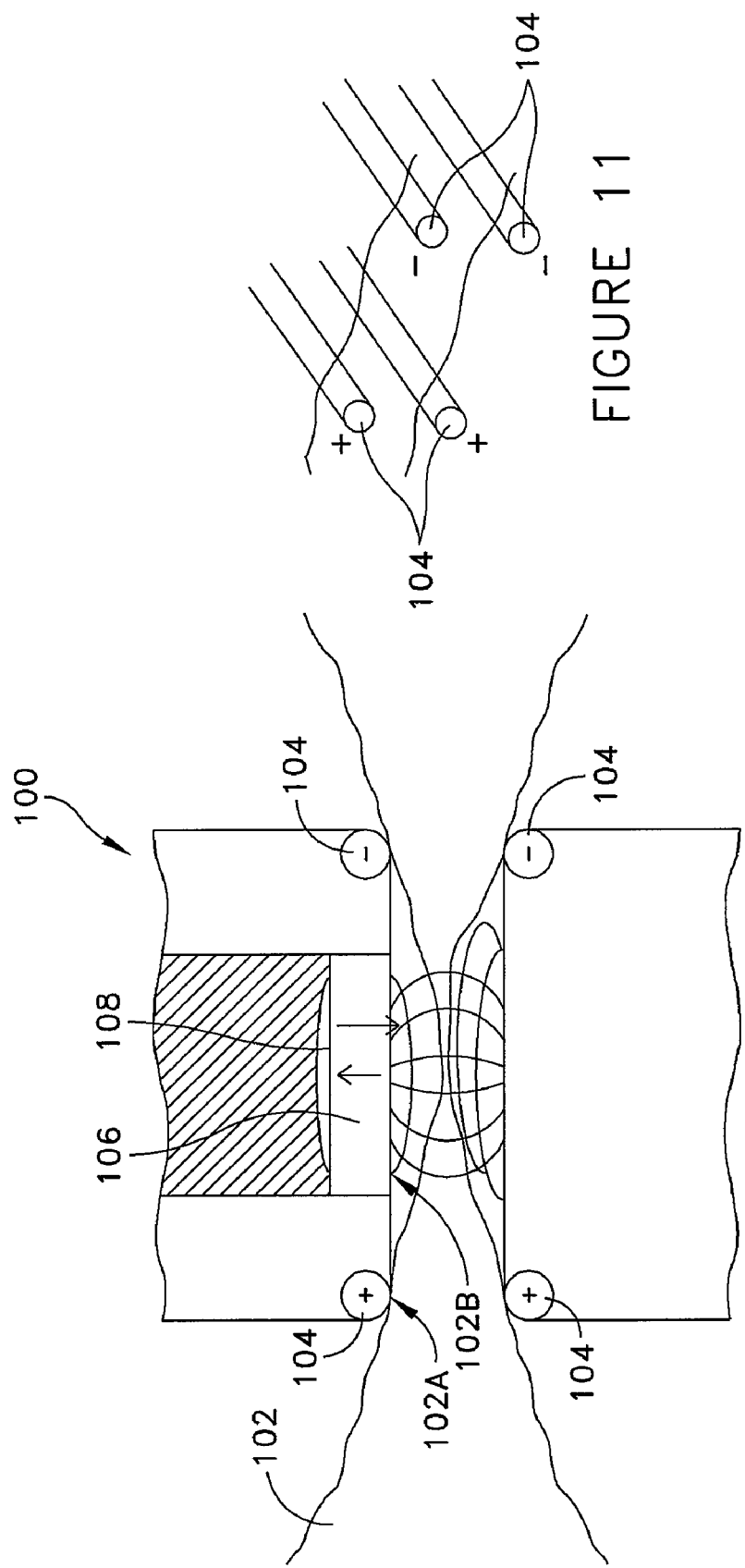

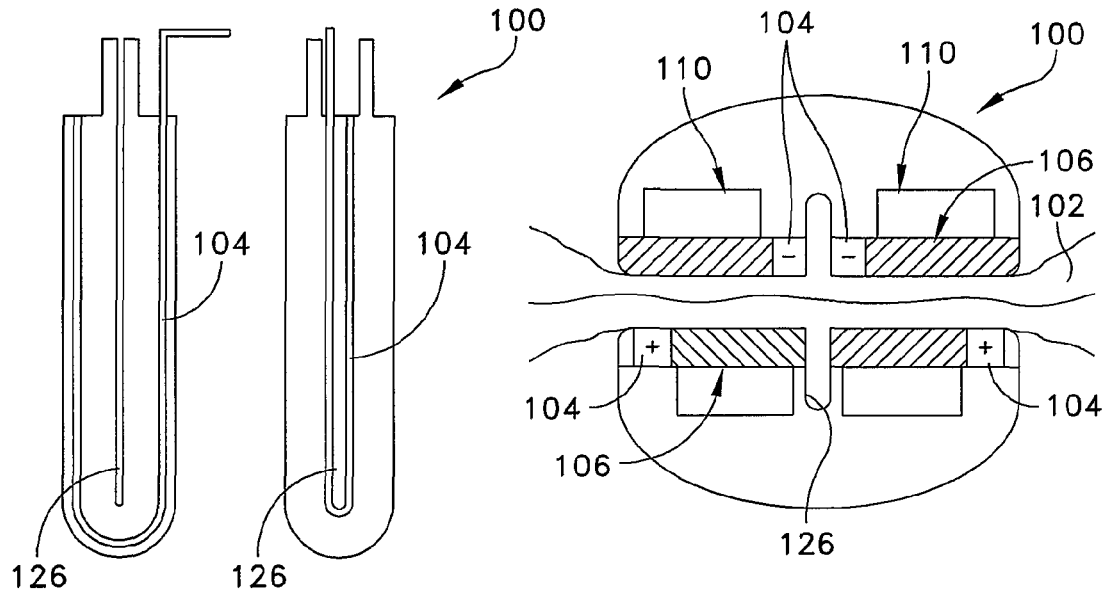
FIGURE 18
FIGURE 19
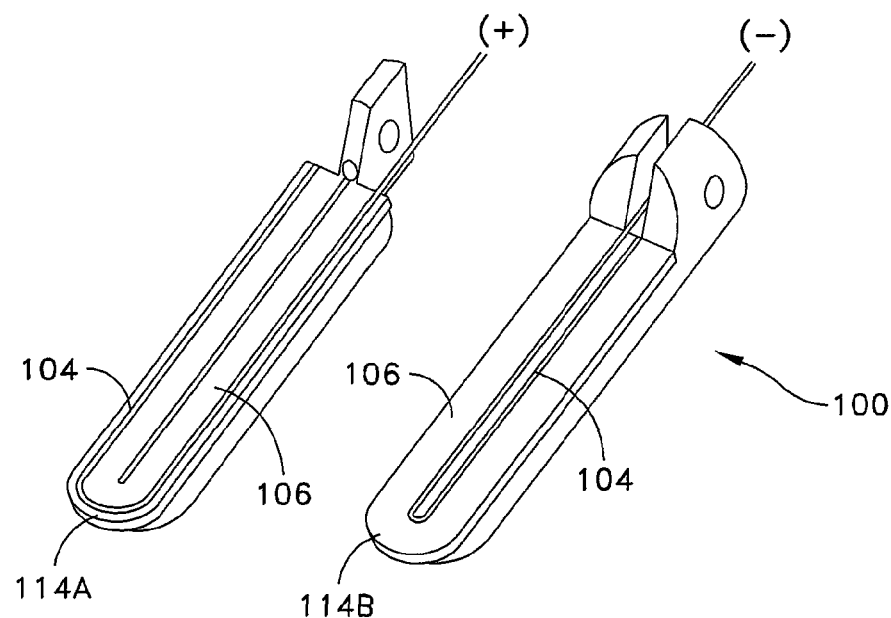
FIGURE 20

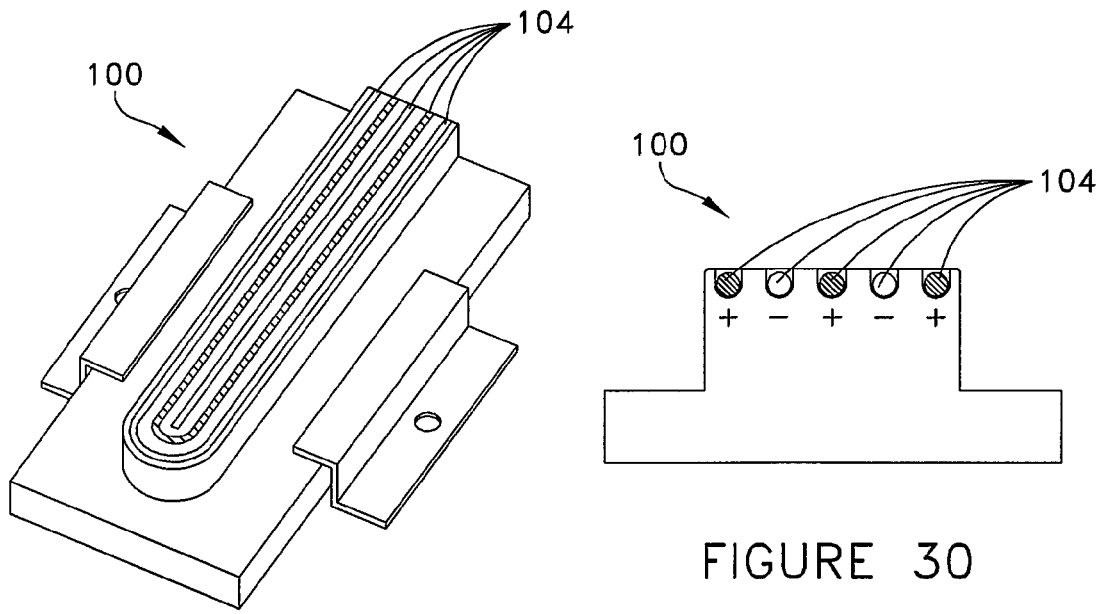
FIGURE 29
FIGURE 30
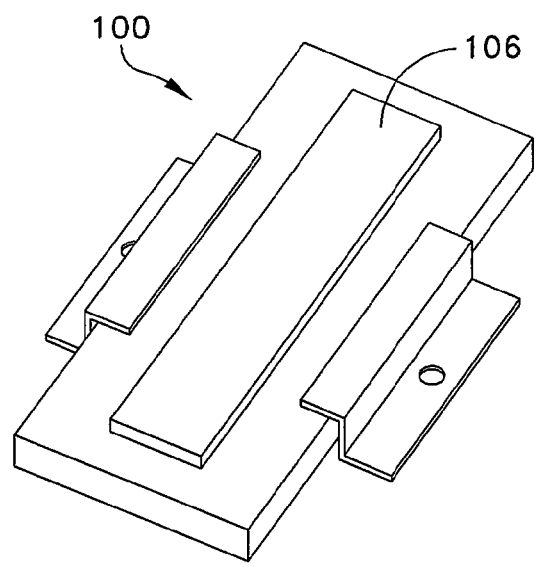
FIGURE 31

APPARATUS FOR ATTACHMENT AND REINFORCEMENT OF TISSUE, APPARATUS FOR REINFORCEMENT OF TISSUE, METHODS OF ATTACHING AND REINFORCING TISSUE, AND METHODS OF REINFORCING TISSUE

REFERENCE TO PENDING PRIOR PATENT APPLICATION

This application claims the benefit under 35 U.S.C. 119(e) of U.S. Provisional Patent Application No. 60/939,602, filed May 22, 2007 by David A. Schechter for RADIO-FREQUENCY TISSUE WELDER WITH POLYMER REINFORCEMENT, which patent application is hereby incorporated herein by reference.

BACKGROUND

Energy-based tissue welding has previously been used with laser, ultrasonic, radio-frequency (RF) energy, or direct thermal cautery technologies. RF tissue welding and other energy based technologies are commercially available to seal and ligate small blood vessels. Some examples include the LigaSure™ ligation device manufactured by Covidien of Mansfield, Mass., the EnSeal® ligation device manufactured by SurgRx® of Redwood City, Calif., the PKS Seal™ device manufactured by Gyrus Group PLC (Olympus of Toyko, Japan) and the Starion™ ligation device manufactured by Starion Instruments of Sunnyvale, Calif. While these devices are indicated solely for vessel ligation, surgeons have attempted to use available vessel sealing technology to weld large tissue structures such as lung and bowel in thoracic and general surgery.

The primary limitation of adapting currently available vessel sealing technology to large tissue structures is marginal or insufficient weld strength. With current vessel sealing technology, RF energy is directed into the target tissue, which in turn is heated at that location. Electrical current, voltage and power may be adjusted using a closed-loop control algorithm based on feedback variables (e.g., impedance, time, temperature, phase, current, power, and voltage, etc.). The mechanism of fusing tissue in opposite layers relies on collagen and elastin protein denaturation in combination with tissue compression to create a physical entanglement of protein chains. The effected tissue is thermally damaged and non-viable. The acute inflammatory response to the thermal injury is minimal, and the proliferative phase (i.e., fibroblast and collagen deposition) of wound healing is believed to last between 2 to 4 weeks, although strength of the effected tissue can be comparative to native tissue in as little as 7 days.

A significant advantage of RF-energy tissue sealers is the ability to reduce the overall device size as compared to larger mechanical suture devices due to design flexibility with wiring and electrodes. This further enables minimally invasive surgery. The necessity of a smaller endoscopic device has led a number of surgeons to use currently available RF vessel sealing technology on pediatric lung resection and on selected complicated thoracic procedures in adults. (See, for example, Albanese C T, Rothenberg S S. Experience with 144 consecutive pediatric thoracoscopic lobectomies. J Laparoendosc Adv Surg Tech A. 2007 June; 17(3):339-41. PMID: 17570785; Rothenberg, S. S., *Thoracoscopy in infants and children: the state of the art*. J Pediatr Surg. 2005 February; 40(2):303-6. PMID: 15750919; Shigemura N, Akashi A, Nakagiri T. *New operative method for a giant bulla: sutureless and stapleless thoracoscopic surgery using the Ligasure system*. Eur J Cardiothorac Surg. 2002 October; 22(4):646-8. PMID: 12297194; Shigemura N, Akashi A, Nakagiri T, Ohta M, Matsuda H. *A new tissue-sealing technique using the Ligasure system for nonanatomical pulmonary resection: preliminary results of sutureless and stapleless thoracoscopic surgery*. Ann Thorac Surg. 2004 April; 77(4):1415-8; discussion 1419. PMID: 15063276; Tirabassi M V, Banever G T, Tashjian D B, Moriarty K P. *Quantitation of lung sealing in the survival swine model*. J Pediatr Surg. 2004 March; 39(3):387-90. PMID: 15017557)

For smaller sections, weld strengths on pulmonary tissue are satisfactory and comparable to conventional methods (e.g., surgical staplers). In a study conducted by Tirabassi et al., lung biopsy sites were created with RF energy (using the Ligasure™ ligation device) or an endoscopic stapler (using the Endo-GIA stapler device.) Both biopsy sites had burst strengths equal to or greater than normal lung tissue in the swine survival model after 7 days (84 cm $H_2O$ and 88 cm $H_2O$, respectively.) The wedge biopsy sections had respective average sizes of 0.87 g and 0.78 g. In studies on larger pulmonary resections (e.g., greater than 1.5 grams), the RF vessel sealing weld strength is reduced significantly as demonstrated by Santini et al. (see Table 1).

TABLE 1

Resistance of RF-based wedge resection margins in porcine lungs to the critical pressure of 82 cm $H_2O$ (60 mm Hg) [SANTINI et al.]

| Percentage of RF-based welds with bursts above critical pressure | Resection size (grams) |
| --- | --- |
| 95 | 0.2 |
| 95 | 0.4 |
| 90 | 0.6 |
| 90 | 0.8 |
| 80 | 1.0 |
| 85 | 1.2 |
| 68 | 1.4 |

Despite the adoption in pediatric thoracic surgery, RF-based tissue welding is generally not used for larger resections, limiting practical use in typical thoracoscopic procedures on adults. Stapling continues to be used for most lung resections. Despite its obvious drawbacks related to size, rigidity, associated complications, and cost, stapling allows simultaneous clamping, severance and closure in adults. However, it may be desirable to increase weld strength and leak resistance in larger resections by reinforcing the weld with a bioabsorbable polymer. Bioabsorbable polymers are currently being used, or investigated for use, in wound closure, scaffolds for tissue engineering, drug delivery systems, cardiovascular, orthopedic, dental, intestinal surgeries, and cosmetic dermatology.

Energy-based tissue welding is currently on the forefront of enabling minimally invasive surgery. Some users have exceeded the limits of existing RF vessel sealing technology for certain types of surgeries. Significant improvements in weld strength may allow larger resections, and may potentially eliminate the need for surgical staples altogether.

SUMMARY OF THE INVENTION

In an embodiment, there is provided apparatus for attachment and reinforcement of tissue, the apparatus comprising an energy applicator positioned adjacent a first tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and a biopolymer applicator disposed at a second tissue contacting surface, the biopolymer applicator configured for housing a biopolymer material at a location adjacent to the target tissue to receive the heat generated by the energy applied to the target tissue so as to allow the biopolymer material to change phase from a solid state to a molten state, and to allow the biopolymer to fill the dried tissue so as to reinforce the portions of the target tissue attached to one another and provide a hermetic seal once the biopolymer cools and returns to the solid state.

In another embodiment, there is provided apparatus for reinforcement of tissue, the apparatus comprising an energy applicator positioned adjacent a first tissue contacting surface, the energy applicator configured to apply an amount of energy to generate heat within a target tissue so as to evaporate intracellular and extracellular water from the target tissue to create dried tissue; and a biopolymer applicator disposed at a second tissue contacting surface, the biopolymer applicator configured for housing a biopolymer material at a location adjacent to the target tissue to receive the heat generated by the energy applied to the target tissue so as to allow the biopolymer material to change phase from a solid state to a molten state, and to allow the biopolymer to fill the dried tissue so as to provide a hemostatic barrier once the biopolymer cools and returns to the solid state.

In yet another embodiment, there is provided a method of attaching and reinforcing tissue, the method comprising applying energy adjacent to tissue surfaces with an energy applicator, wherein the application of the energy is configured to generate an amount of heat within the tissue surfaces so as to evaporate intracellular and extracellular water from the target tissue to create dried tissue, and denature at least one of collagen and elastin within the tissue surfaces to attach portions of the tissue surfaces to one another; and applying a biopolymer material into the tissue surfaces with a biopolymer applicator disposed on a housing in connection with the energy applicator, wherein the application of the biopolymer material includes housing the biopolymer material at a location adjacent to the tissue surfaces to receive the heat generated by the energy applied to the target tissue so as to allow the biopolymer material to change phase from a solid state to a molten state, and to allow the biopolymer to fill the dried tissue so as to reinforce the portions of the target tissue attached to one another and provide a hermetic seal once the biopolymer cools and returns to the solid state.

In still another embodiment, there is provided method of reinforcing tissue, the method comprising applying energy adjacent a tissue surface with an energy applicator, wherein the application of the energy is configured to generate an amount of heat within a target tissue so as to evaporate intracellular and extracellular water from the target tissue to create dried tissue; and applying a biopolymer material into the target tissue with a biopolymer applicator disposed on a housing in connection with the energy applicator, wherein the application of the biopolymer includes housing the biopolymer material at a location adjacent to the target tissue to receive the heat generated by the energy applied to the target tissue so as to allow the biopolymer material to change phase from a solid state to a molten state, and to allow the biopolymer to fill the dried tissue so as to provide a hemostatic barrier once the biopolymer cools and returns to the solid state.

Other embodiments are also disclosed.

BRIEF DESCRIPTION OF THE DRAWINGS

Illustrative embodiments of the invention are illustrated in the drawings, in which:

FIGS. 1-8 illustrate various exemplary embodiments of apparatus for attachment and reinforcement, or only reinforcement, of tissue;

FIG. 9 illustrates tissue having reinforced areas with a biopolymer material divided apart using apparatus for reinforcement of tissue;

FIG. 10 is a schematic illustration of apparatus having an radio frequency energy source for attachment and reinforcement of tissue;

FIG. 11 is an illustration of one electrode configuration;

FIGS. 16-24 illustrate embodiments of jaw effectors for attachment and reinforcement of tissue with radio frequency energy sources;

FIGS. 25-32 illustrate various devices having energy applicators and biopolymer applicators for reinforcement of tissue and for creating a hemostatic barrier on adjacent exposed tissue parenchyma on tissues such as liver during resection.

Figure 1:
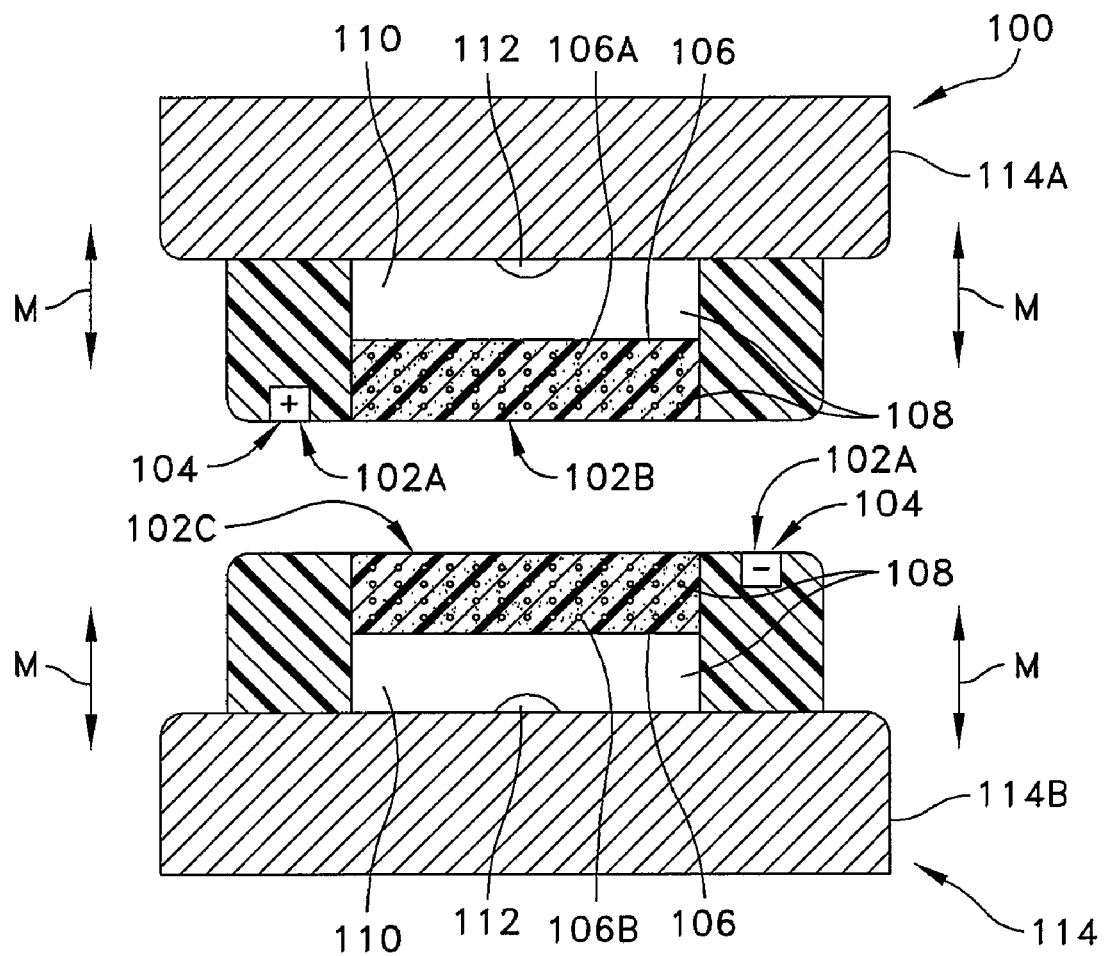
Figure 2:
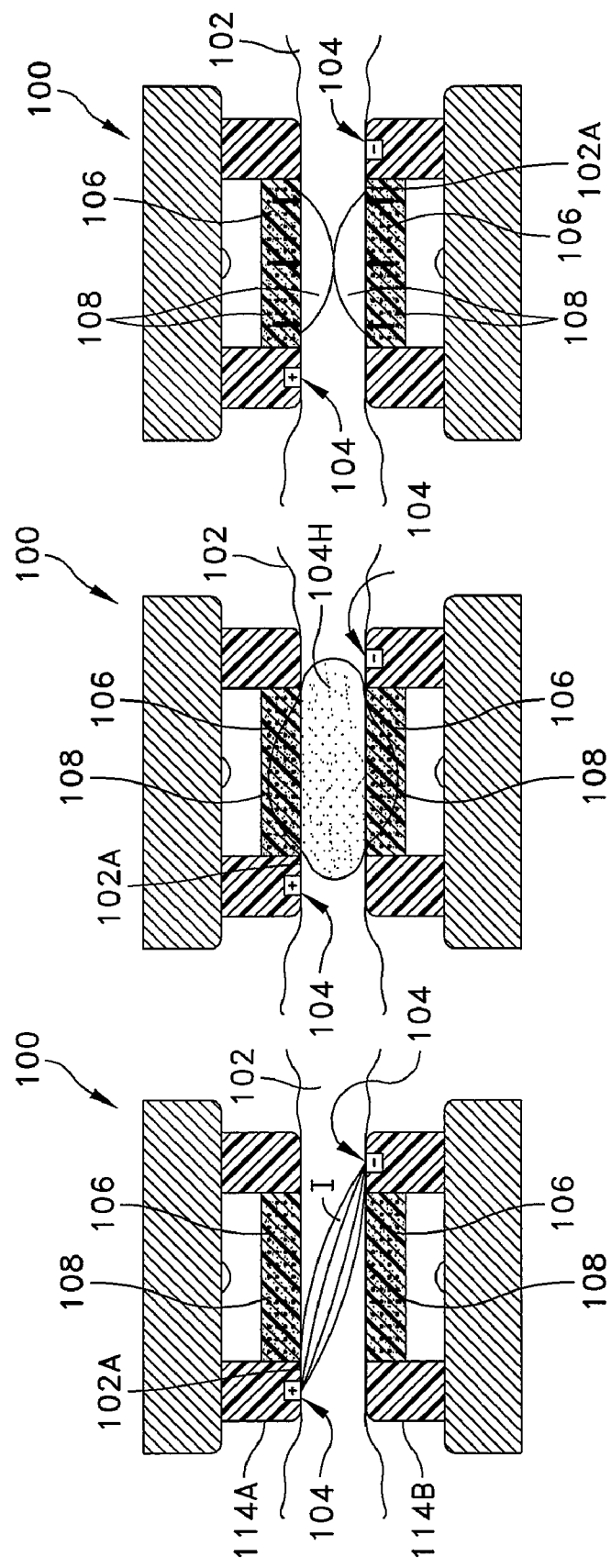
Figure 12:
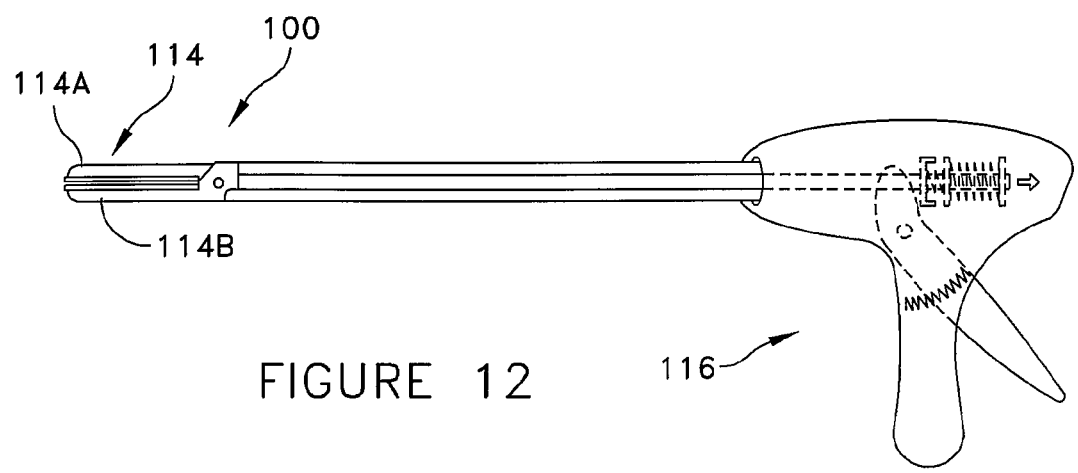
FIGS. 12-15 illustrate various clamping mechanisms for selectively applying pressure to tissue.
Figure 13:
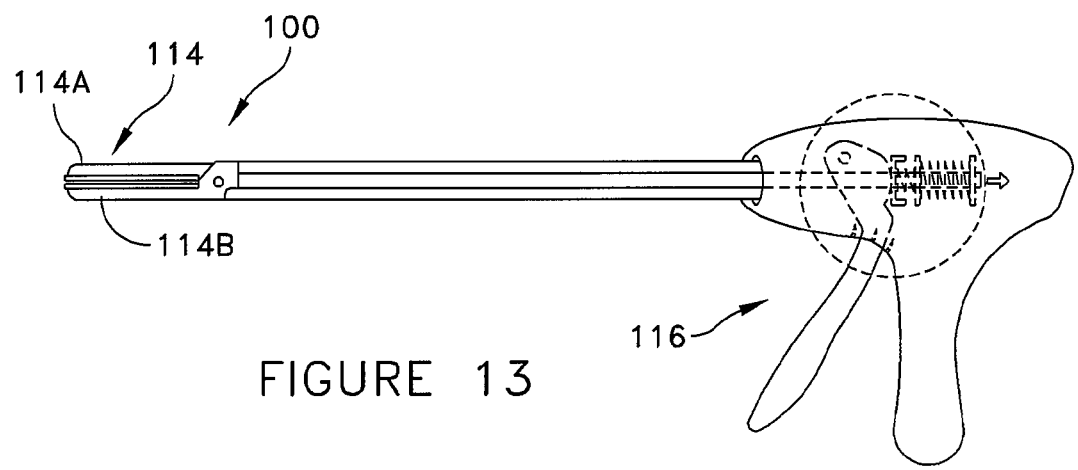
Figure 14:
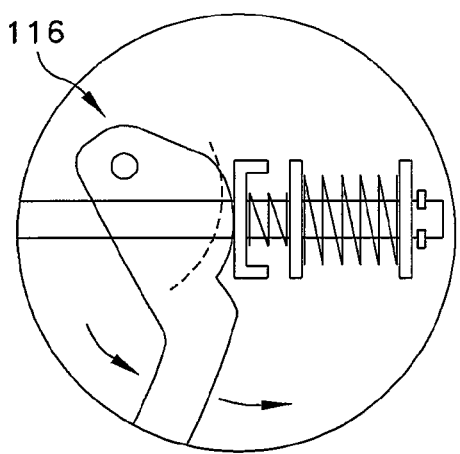

In the following description, reference is made to the accompanying drawings that form a part of the present disclosure, and in which are shown, by way of illustration, specific embodiments of the invention. These embodiments are described in sufficient detail to enable those skilled in the art to practice the invention, and it is to be understood that other embodiments may be utilized and that structural and other changes may be made without departing from the scope of the present invention. The present disclosure is, therefore, not to be taken in a limiting sense. The present disclosure is neither a literal description of all embodiments of the invention nor a listing of features of the invention that must be present in all embodiments.

Numerous embodiments are described in this patent application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with various modifications and alterations. Although particular features of the present invention may be described with reference to one or more particular embodiments or figures, it should be understood that such features are not limited to usage in the one or more particular embodiments or figures with reference to which they are described.

The terms "an embodiment", "embodiment", "embodiments", "the embodiment", "the embodiments", "an embodiment", "some embodiments", and "one embodiment" mean "one or more (but not all) embodiments of the present invention(s)" unless expressly specified otherwise.

The terms "including", "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The terms "a", "an" and "the" mean "one or more", unless expressly specified otherwise.

Headings of sections provided in this patent application and the title of this patent application are for convenience only, and are not to be taken as limiting the disclosure in any way.

DETAILED DESCRIPTION

In an embodiment, a low-molecular weight, bioabsorbable polymer may be introduced to, and penetrate into, thermally denatured collagen and elastin thereby increasing the weld strength. The ability to infuse a low molecular weight polymer and structurally reinforce thermally treated tissue has the potential to enable a vast array of surgical procedures. Efficient infusion of low molecular weight polymers into tissues can be used to improve structural rigidity of tissues, to provide hemostatic barriers, or to physically attach grafts and meshes. Applications of infusion of low molecular weight polymers may range from improving sphincter control in patients with urinary incontinence, reducing blood loss in liver resection, creating rigidity of the uvula in somnoplasty, or improving methods of affixing hernia meshes as well as numerous other applications in cosmetic surgery where bulking is required.

Referring to FIGS. 1-8, there is shown an apparatus 100 for attachment and reinforcement of tissue 102. Apparatus 100 may include an energy applicator 104 positioned adjacent a first tissue contacting surface 102A. Energy applicator 104 may be configured to apply an amount of energy to generate heat within target tissue 102 so as to evaporate intracellular and extracellular water from target tissue 102 to create dried tissue. In an embodiment, apparatus 100 may apply energy to denature at least one of collagen and elastin within target tissue 102 to attach portions of the target tissue together. In one embodiment, the applied energy is configured to denature collagen. In another embodiment, the applied energy is configured to denature both collagen and elastin.

Still referring to FIGS. 1-8, and in an embodiment, a biopolymer applicator 106 may be disposed at a second tissue contacting surface 102B. In one embodiment, surface 102A and surface 102B may be coextensive with one another. In another embodiment, surface 102A and surface 102B may be adjacent to one another on a single portion, such as an end effector, of a device. In an embodiment, surface 102A and surface 102B may be located on separate portions of a device, such as on opposed jaw portions. Biopolymer applicator 106 may be configured for housing a biopolymer material 108 at a location adjacent to the target tissue 102. This allows the biopolymer material 108 to receive the heat generated by the energy applied to target tissue 102 so as to allow biopolymer material 108 to change phase from a solid state to a molten state. This also allows biopolymer material 108 to fill the dried tissue so as to reinforce the portions of target tissue 102 attached to one another and provide a hermetic seal once biopolymer material 108 cools and returns to the solid state.

As heat is generated within tissue 102, it is thermally transferred into porous plate 106 located within a jaw inner face or tissue-contacting region. Porous plate 106 is embedded with biopolymer 108, such that biopolymer 108 is contained within the pores of plate 106. As the porous plate is heated, the biopolymer changes from a solid to a molten state and is drawn or wicked into target tissue 102 by capillary action. The molten low viscosity bioabsorbable polymer 108 fills the voids between the denatured collagen and elastin thereby reinforcing the weld and providing a hermetic seal once the polymer has cooled.

Energy applicator 106 may be configured to provide various types of energy. In an embodiment, energy applicator 106 is a radio-frequency applicator. In another embodiment, energy applicator 106 is a ultrasonic applicator. In one embodiment, energy applicator 106 is a laser applicator. In an embodiment, energy applicator 106 is a microwave applicator. Energy applicator 106 may be configured to emit other types of energy.

Referring again to FIG. 2, biopolymer applicator 106 may include one or more porous plates 106. Porous plate 106 is generally provided to be thermally stable up to a temperature above 200° C. In one embodiment, porous plate 106 is a high temperature thermoplastic. For example, the high temperature thermoplastic may be polytetrafluoroethylene (PTFE). In another embodiment, porous plate 106 is a porous ceramic. In one embodiment, porous plate 106 is a porous metal. The porous metal of porous plate 106 may be configured as an electrode for energy applicator 104 using radio-frequency energy. In an alternative embodiment, porous plate 106 may include a metal surface as an electrode for energy applicator 104 using radio-frequency energy. The symbols (+) and (−) are for reference only and are intended to diagrammatically demonstrate bipolar modes of energy delivery. In another embodiment, energy applicator 104 may use other modes of energy delivery.

Referring now to FIG. 1, and in an embodiment, biopolymer applicator 106 may include a reservoir 110 adjacent to biopolymer material 108 embedded within porous plate 106. Reservoir 110 may containing an additional amount of biopolymer material 108. Reservoir 110 may include a thermal regulator 112, which may be configured to control the change phase of biopolymer material 108 from the solid state to the molten state. Reservoir 110 may include a tube (FIG. 8) along a length of an endoscopic shaft in connection to biopolymer applicator 106.

In another embodiment, porous plate 106 and polymer reservoir 110 may be separately thermally regulated (i.e., heated or cooled). The physical state of biopolymer material 108 may be controlled from a melt to a solid, or vice versa.

In one exemplary embodiment, thermal regulator 112 may include a resistive element to directly heat the biopolymer material and, in turn, control the change phase of biopolymer material 108 from the solid state to the molten state. In another embodiment, thermal regulator 112 may include at least one of a gas heat exchange system and a liquid heat exchange system to thermally regulate biopolymer material 108. Alternatively, thermal regulator 112 may include a thermoelectric cooling system to thermally regulate the biopolymer material. In still another embodiment, thermal regulator 112 may include a direct cooling system to thermally regulate the biopolymer material. Optionally, the direct cooling system may include a saline infusion to thermally regulate biopolymer material 108.

Temperature regulation may provide the ability to thermally regulate reservoir 110, which may be located in a handset portion, and to deliver molten biopolymer material 108 to tissue contacting surface 102B without having to reload polymer or polymer cartridges. This provides the ability to provide a number of consecutive applications.

In one embodiment, reservoir 110 may be configured to actively pump biopolymer material 108 across porous plate 106. In an embodiment, biopolymer cartridges may provide biopolymer material 108. Reservoir 110 may be configured to receive the biopolymer cartridges to provide biopolymer material 108 to biopolymer applicator 106.

Biopolymer material 108 may have many different properties. For example, and in an embodiment, biopolymer material 108 is electrically non-conductive. Biopolymer material 108 may include polycaprolactone (PCL). Biopolymer material 108 may be a polycaprolactone (PCL) copolymer. In one embodiment, biopolymer material 108 may be selected to have one or more properties including, but not limited to, a molecular weight less than 3000 MW, a melt temperature between about 37° C. and 200° C., and a melt viscosity less than about 1000 Centipoise (cps). Alternatively, biopolymer material 108 may have a glass transition temperature of about 60° C. For example, polycaprolactone (PCL) is a very well-studied bioabsorbable, aliphatic polyester with a wide range of physicochemical properties available by copolymerization. Polycaprolactone (PCL) is a semicrystalline polymer with a low glass transition temperature (about 60° C.) Among various bioabsorbable polymers, polycaprolactone (PCL) is relatively hydrophobic and has a very slow degradation rate. In another embodiment, biopolymer material 108 may be a non-bioabsorbable thermoplastic or paraffin wax. The thermoplastic or wax materials may be selected with melt temperatures between 37° C. and 200° C., and melt viscosities less than 1000 centipoise.

Biopolymer material 108 may include a bioabsorbable dye. Visible feedback is provided when biopolymer material 108 with the bioabsorbable dye has been absorbed into target tissue 102. In an embodiment, bioabsorbable dye 108 is methylene blue.

First tissue contact surface 102A and second tissue contacting surface 102B may be adjacent to one another. Alternatively, first tissue contact surface 102A and second tissue contacting surface 102B may be located remotely from one another. For example, first tissue contact surface 102A and second tissue contacting surface 102B of energy applicator 104 may each be positioned on a set of jaws 114. First tissue contact surface 102A and second tissue contacting surface 102B may be adjacent to one another on one jaw 114A or 114B of the set of jaws 114. For apparatus 100 including jaws 114, an example of relative movement is denoted by reference character M in FIG. 1. First tissue contact surface 102A and second tissue contacting surface 102B may be located remotely from one another on opposed jaws 114A, 114 of the set of jaws 114.

Biopolymer applicator 106 may include a third tissue contacting surface 102C. In an embodiment, second tissue contacting surface 102B may include a first porous plate 106A and third tissue contacting surface 102C may include a second porous plate 106B. Second tissue contacting surface 102B and third tissue contacting surface 102C may be located remotely from one another on opposed jaws 114A, 114B of the set of jaws 114.

As illustrated in FIGS. 2A-2C, and in an embodiment, porous plate 106 may be electrically non-conductive and located on tissue contacting surface 102A of at least one of the grasping jaws. As illustrated in FIG. 2A, grasping jaws 114 may apply tissue compression force. Porous plate 106 is in direct contact with the heated target tissue, providing a path of thermal conduction into biopolymer 108. Electrodes 104 may be configured such that current (see reference character I in FIG. 2A) flows in a side-to-side (i.e., parallel) manner across the width or length of jaw 114A. This can be achieved using electrodes offset from each other along the width or length of grasping jaw 114, either on the same tissue-contacting surface or on opposing tissue contacting surfaces. Offset is defined as an electrode configuration, where electrodes located one jaw are not geometrically or directly opposed to an electrode of a different potential or polarity located on the corresponding mating jaw. An offset configuration can also exist with electrodes located on only one jaw surface, such that the electrodes of differing electrical potentials are spaced apart with current flowing substantially planar to the clamped tissue (FIG. 3). Additionally, offset configurations can include a plurality of electrode sets (FIG. 4). As shown in FIG. 2B, heat 104H is generated between jaws 114. In FIG. 2C, there is shown biopolymer 108 wicked into tissue 102.

Referring to FIGS. 16-20, and in an embodiment, electrodes 104 are offset and configured as an inner electrode and outer u-shaped ring. The inner electrode 104 and outer electrode 104 are arranged such that the linear distance from one another remains consistent with reference to plane of clamped tissue 104. Outer electrode 104 is located on at least one tissue contacting surface and inner electrode 104 is located on at least one of the tissue contacting surface (FIGS. 18-20.) Both inner and outer electrodes 104 may be disposed on the same tissue contacting surface and the opposing tissue contacting surface corresponding to porous plate 106. This provides simplicity of design and ease of manufacture although functionally the inner and outer electrodes may reside on opposing surfaces and the porous plate may be on one or both tissue contacting surfaces.

In an another embodiment, porous plate 106 is electrically conductive and located on the tissue contacting surface of at least one of the grasping jaws, and may be located on both jaws with each porous plate 106 electrode having opposite polarity (FIG. 7). Electrical current is conducted through porous plate 106 and into tissue 102. As illustrated in FIG. 6, and in one embodiment, only one of jaws 114A, 114B need contain electrically conductive porous plate 106.

Grasping jaws 114 may include pressure controlled clamping of target tissue 102. Jaws 114A, 114B may grasp and approximate tissue with a low pressure or low force to allow for positioning and tissue manipulation with out excessive tissue damage (for example, less than 1 kgf/cm$^2$) and allow for a high pressure clamping for tissue welding (for example, about 5 to 10 kgf/cm$^2$). Alternatively, the grasping mechanism may be designed such that energy can be applied initially at the low pressure set-point and transitioned to the high pressure set-point during activation. This can allow for improved incorporation of elastin into the tissue weld as high pressure may prematurely tear the elastin fibers and weaken the tissue weld.

Figure 15:
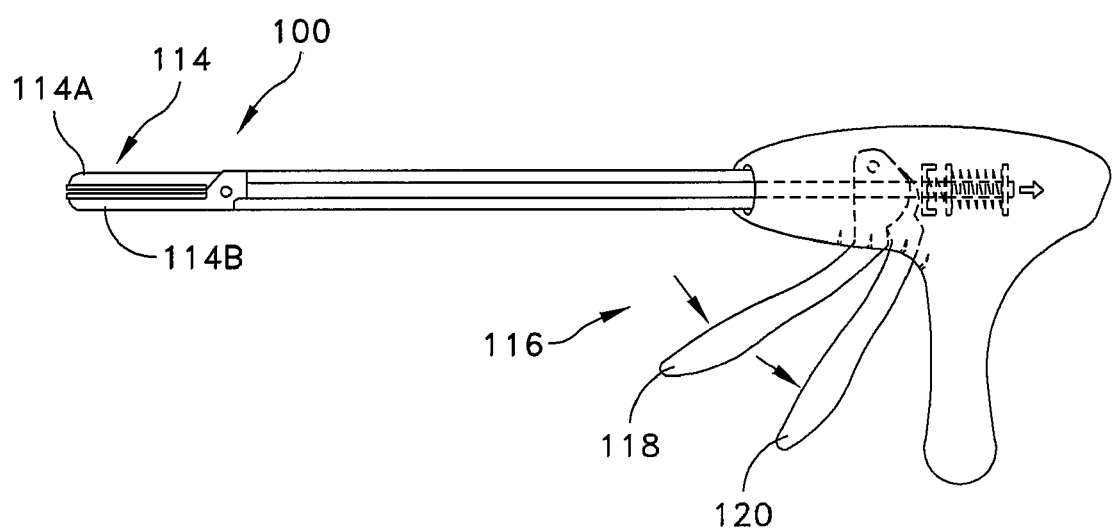
Figure 16:
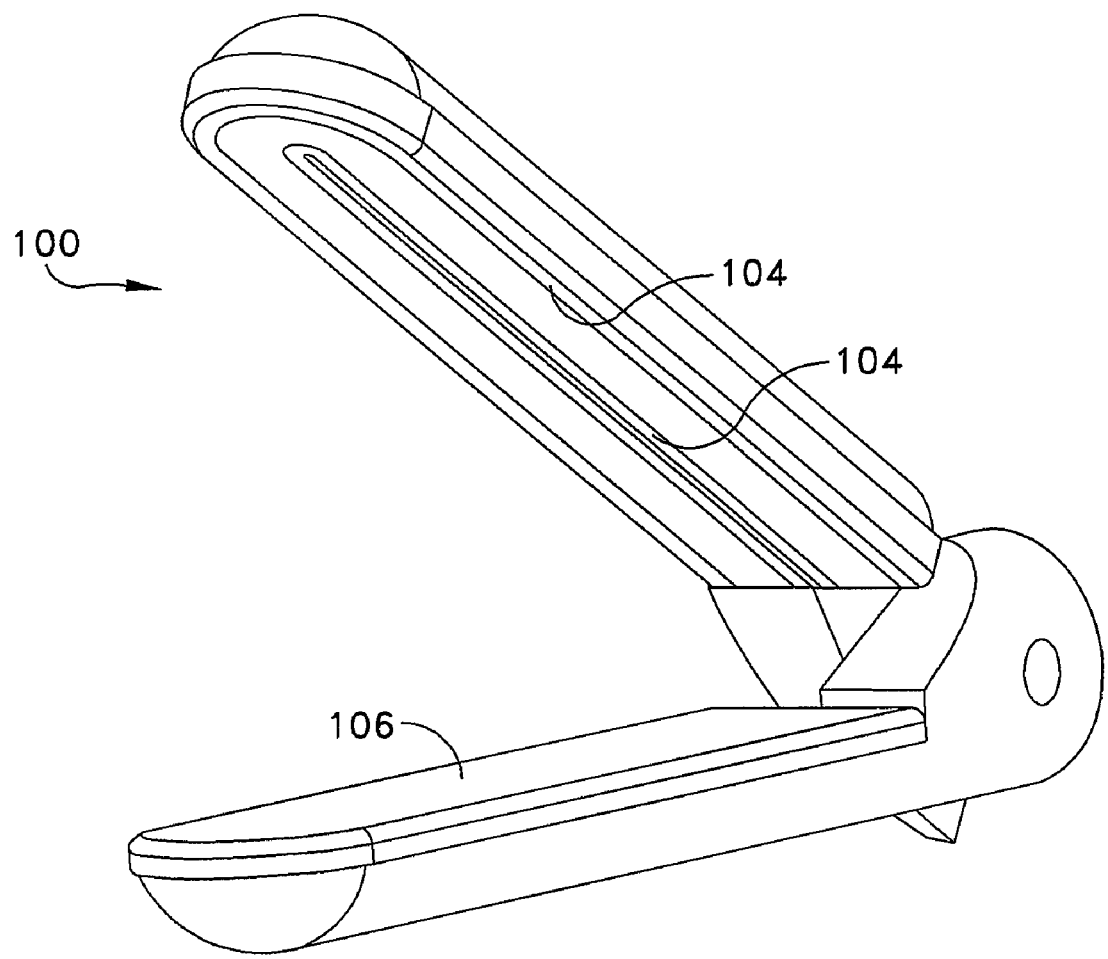
Figure 17:
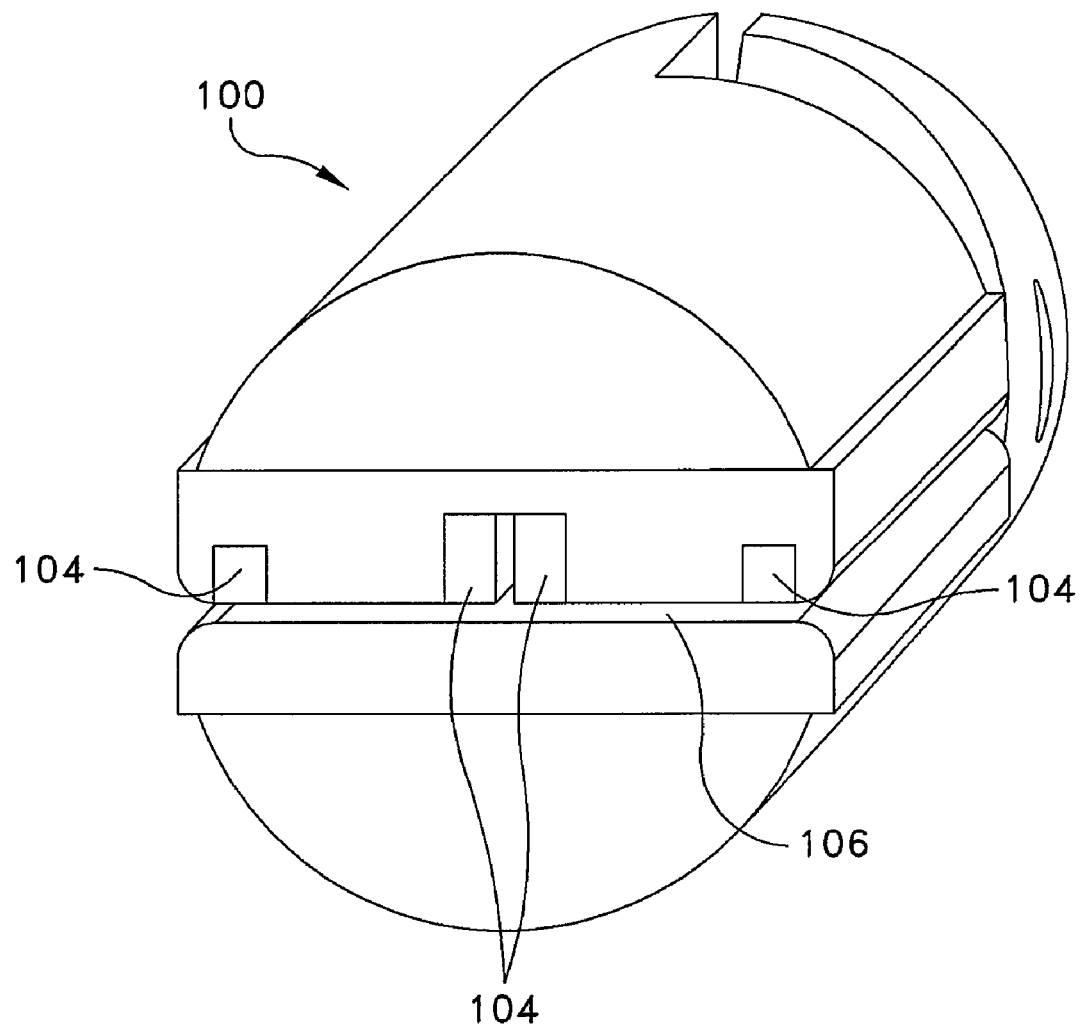
Figure 21:
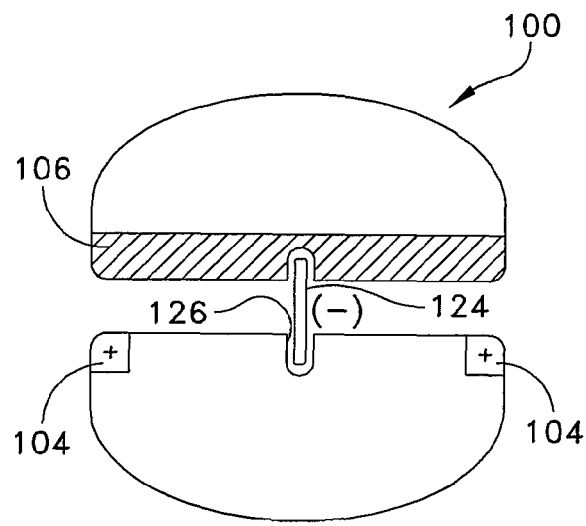
Figure 22:
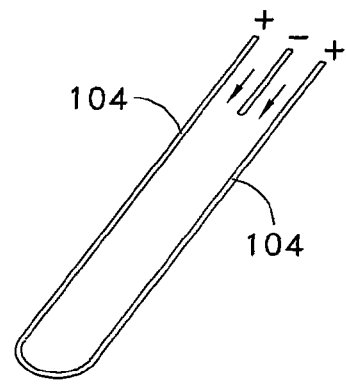
Figure 23:
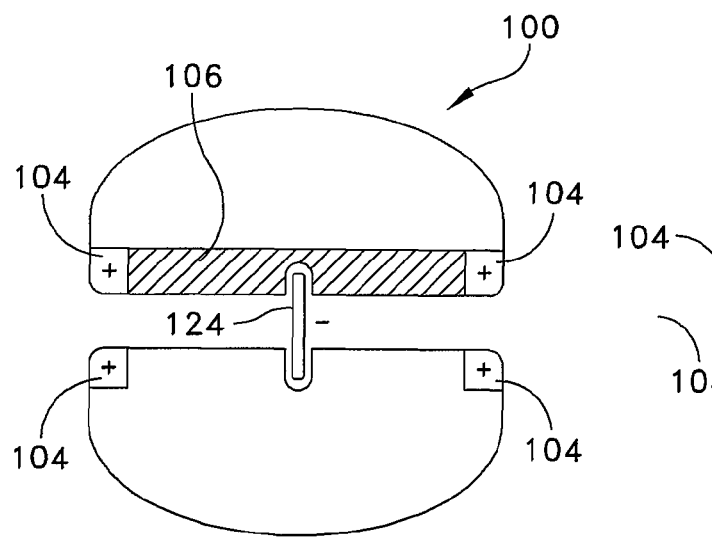
Figure 24:
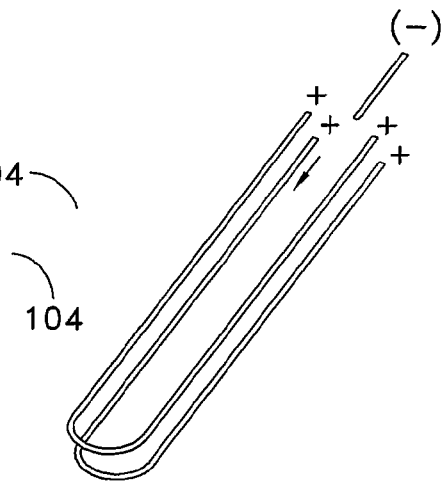
Figure 25:
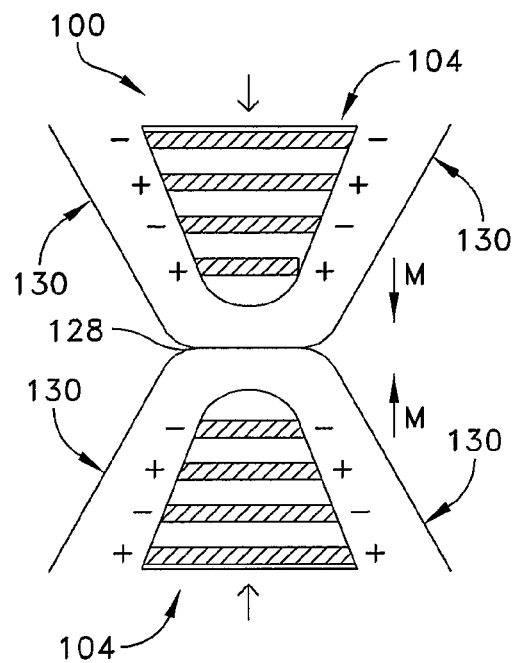
Figure 26:
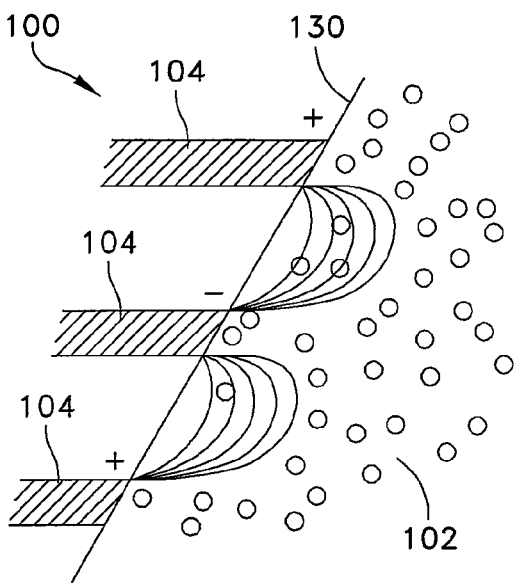
Figure 27:
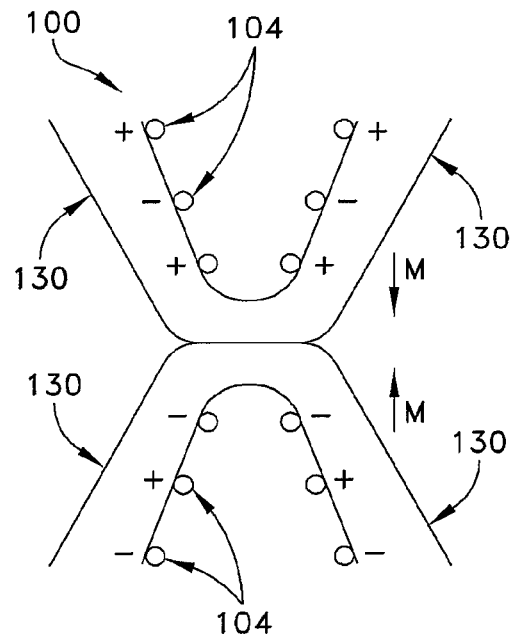
Figure 28:
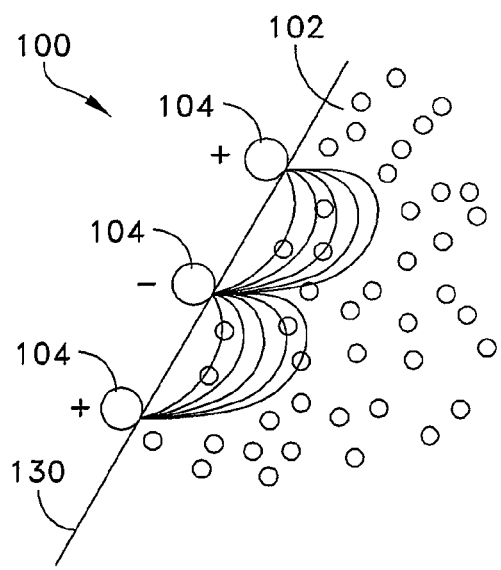

Referring still to FIGS. 12-15, there is shown a pressure controller 116 in operable connection with the set of jaws 114. Pressure controller 116 may include a low pressure setting at location 118 and a high pressure setting at location 120 (FIG. 15). Low pressure setting may be configured to allow jaws 114A, 114B to apply a low amount of pressure so as to grasp and approximate tissue without excessive damage to the tissue. High pressure setting may be configured to allow the jaws 114A, 114B to apply a high amount of pressure so as to clamp the tissue for welding with energy applicator 104 and biopolymer applicator 106. For example, pressure controller 116 may include, at the high pressure setting at location 118, an initial set-point during initial activation of energy applicator 104. At location 120, pressure controller may also provide an escalating pressure up to a maximum set-point subsequent to initial activation of energy applicator 104.

In one embodiment, biopolymer applicator 106 provides a delivery mechanism for passively delivering biopolymer 108 into thermally welded tissue to structurally reinforce the weld. There may be provided two opposing jaw members 114 A, 114B, which are capable of approximating and clamping target tissue 102. Bipolar radio-frequency energy may be conducted through target tissue 102 to cause localized heating. Energy may be applied up to the point where the intracellular and extracellular water is evaporated from target tissue 102 and the collagen and elastin are denatured. This initial coagulation necrosis may be described as a loose entanglement of the denatured collagen and elastin fibers.

As heat is generated within tissue 102, it is thermally transferred into porous plate 106 located within inner face of jaw 114 or into another tissue-contacting region 102B, 102C. Porous plate 106 is embedded with biopolymer 108, such that biopolymer 108 is contained within the pores of plate 106. As porous plate 106 is heated, biopolymer 108 changes from a solid to a molten state and is drawn or wicked into target tissue 106 by capillary action. The molten low viscosity bioabsorbable polymer fills the voids between the denatured collagen and elastin thereby reinforcing the weld and providing a hermetic seal once polymer 108 has cooled.

As illustrated in exemplary embodiments shown in FIGS. 21-24, a knife 124 may be provided for division of target tissue 102. At least one of jaws 114A, 114B may form a knife channel 126 therein containing knife 124, wherein the knife extends from knife channel 126. In an embodiment, knife 124 is an electrode portion of a radio-frequency applicator of energy applicator 104.

Figure 32:
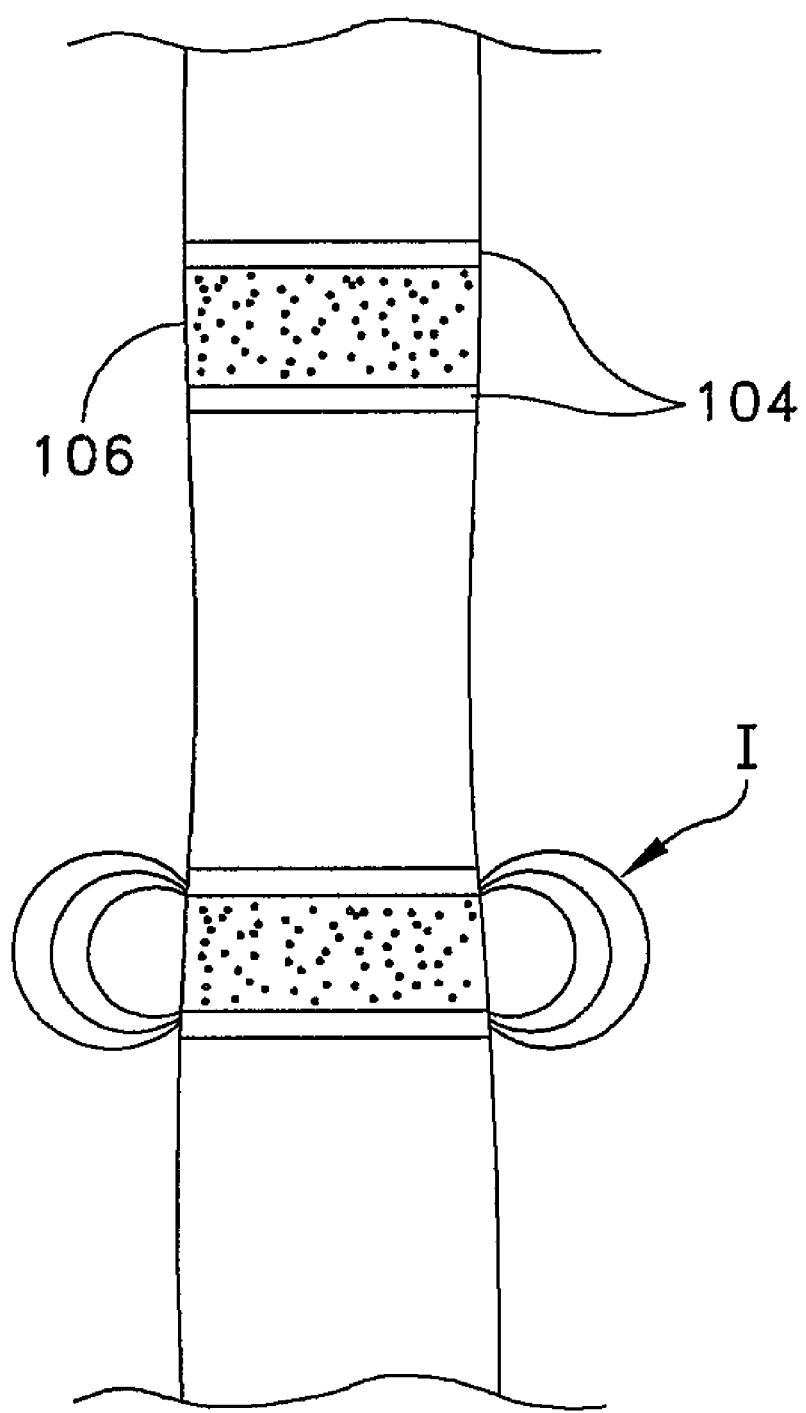

Apparatus 100 may be provided in various configurations for a variety of procedures. In an embodiment, energy applicator 104 and biopolymer applicator 106 may be configured for liver resection or solid organ resection. The parenchymal tissue is divided by blunt dissection or by a crush technique by mechanism of closing a hinged pair of jaws and physically dividing the tissue. Energy applicator and biopolymer applicator are configured on the sides of the jaws surface in order to deliver biopolymer to the exposed parenchymal tissue adjacent to the device and to create a hemostatic barrier. As illustrated in FIGS. 25-28, a hinged portion 128, energy applicator and biopolymer applicator may be provided on apparatus 100 to engage with tissue or parenchyma 130 for liver resection or solid organ resection. FIGS. 29-31 illustrate an embodiment of apparatus 100 with energy applicator 104 and biopolymer applicator 106. As illustrated in FIG. 32, energy applicator 104 and biopolymer applicator 106 may be configured to heat and to deliver biopolymer in an annular or ring-shaped fashion. This is particularly useful for procedures where creating structural rigidity of an annular or ring-shaped section of tissue is desired such as for improving sphincter control in patients with urinary incontinence or creating rigidity of the uvula in somnoplasty.

The inner electrode deploys distally. Attached to the distal end of the inner electrode may be a knife edge for dividing tissue. Energy can be delivered as the inner electrode is deployed distally or after the inner electrode is fully deployed. This electrical configuration is first described by Wappler, et al. in U.S. Pat. No. 2,031,682. Other patents that describe deployable knife/electrodes are 6652521 and 7087054.

In another embodiment, energy applicator 104 may be positioned adjacent a first tissue contacting surface 102A and may be configured to apply an amount of energy to generate heat within target tissue 102. The heat evaporates intracellular and extracellular water from target tissue 102 to create dried tissue. Biopolymer applicator 106 may be disposed at second tissue contacting surface 102B. Biopolymer applicator 106 may be configured for housing biopolymer material 108 at a location adjacent to target tissue 102. The heat generated allows biopolymer material 108 to change phase from a solid state to a molten state. Biopolymer material 108 fills the dried tissue so as to provide a hemostatic barrier once biopolymer material 108 cools and returns to the solid state. In applications for creating a hemostatic barrier, or to provide structural rigidity of surrounding native tissue, direct tissue compression is not required. An electrode or energy source may be simply placed in contact with the target tissue causing desiccation. The porous plate remains adjacent, and in contact with, target tissue 102 to deliver the molten biopolymer material 108.

Figure 33:
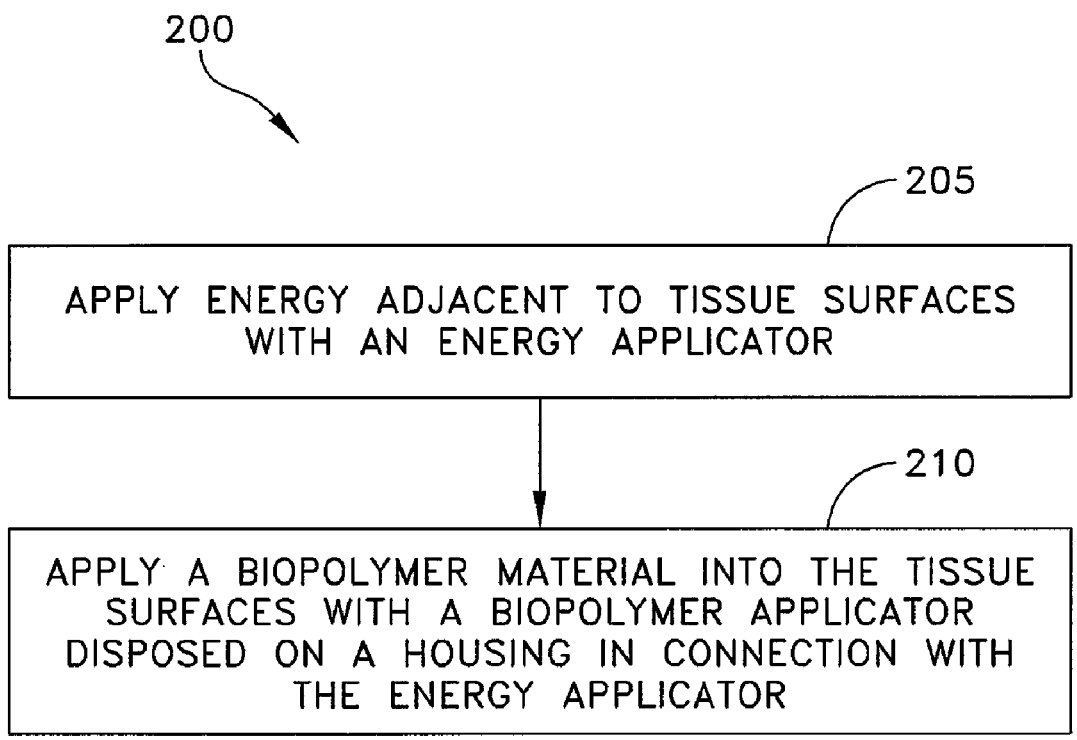
FIGS. 33 and 34 illustrate exemplary methods of applying energy and applying a biopolymer material into tissue.

Referring to FIG. 33, there is provided a method 200 of attaching and reinforcing tissue. Method 200 may include applying 205 energy adjacent to tissue surfaces with an energy applicator. Application of the energy may be configured to generate an amount of heat within the tissue surfaces. The heat evaporates intracellular and extracellular water from the target tissue to create dried tissue. The heat also denatures collagen and elastin within the tissue surfaces to attach portions of the tissue surfaces to one another. Method 200 may further include applying 210 a biopolymer material into the tissue surfaces with a biopolymer applicator disposed on a housing in connection with the energy applicator. Application of the biopolymer material may include housing the biopolymer material at a location adjacent to the tissue surfaces to receive the heat generated by the energy applied to the target tissue. This heat allows the biopolymer material to change phase from a solid state to a molten state. The heat also allows the biopolymer to fill the dried tissue so as to reinforce the attach portions of the tissue portions and provide a hermetic seal once the biopolymer cools and returns to the solid state.

Figure 34:
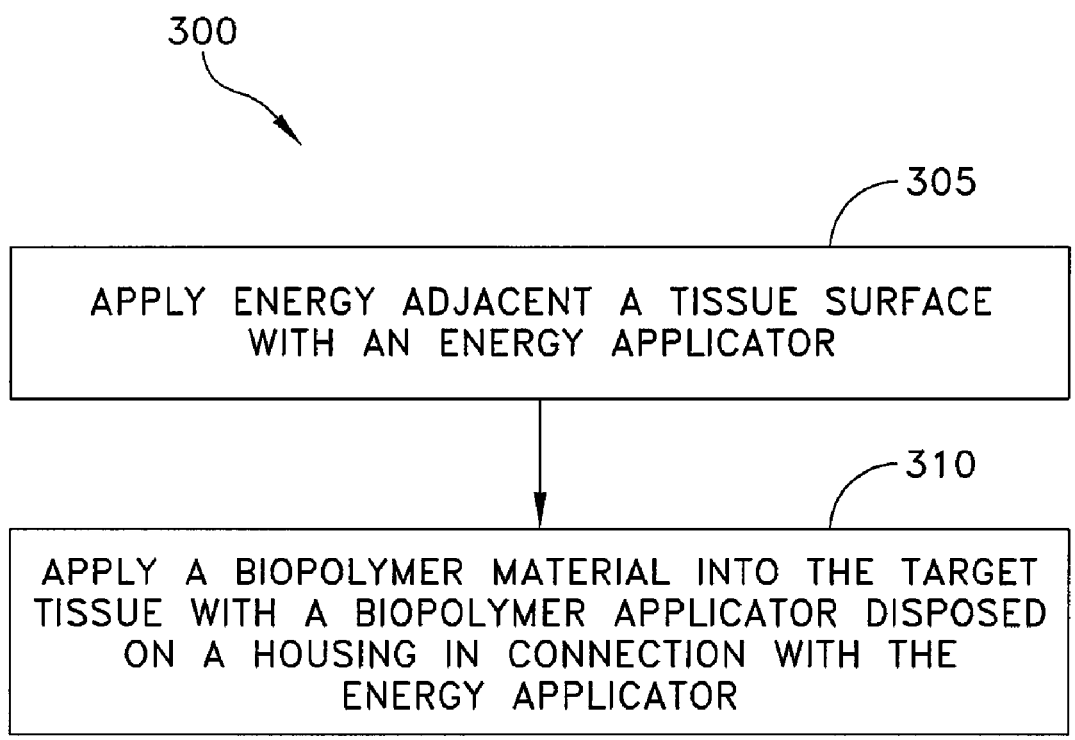

Referring to FIG. 34, there is provided a method 300 of reinforcing tissue. Method 300 may include applying 305 energy adjacent a tissue surface with an energy applicator. Application of the energy may be configured to generate an amount of heat within a target tissue. The heat evaporates intracellular and extracellular water from the target tissue to create dried tissue. Method 300 may further include applying 310 a biopolymer material into the target tissue with a biopolymer applicator disposed on a housing in connection with the energy applicator. Application of the biopolymer includes housing the biopolymer material at a location adjacent to the target tissue to receive the heat generated by the energy applied to the target tissue. The heat allows the biopolymer material to change phase from a solid state to a molten state. The biopolymer fills the dried tissue so as to provide a hemostatic barrier once the biopolymer cools and returns to the solid state.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. Further, it will be apparent to those of skill in the art that numerous changes may be made in such details without departing from the spirit and the principles of the invention.

What is claimed is:

1. Apparatus for attachment and reinforcement of tissue, the apparatus comprising:
   an energy applicator positioned adjacent a first tissue contacting surface, the energy applicator configured to apply an amount of energy to generate heat within a target tissue so as to evaporate intracellular and extracellular water from the target tissue to create dried tissue, and denature at least one of collagen and elastin within the target tissue to attach portions of the target tissue together; and
   a biopolymer applicator disposed at a second tissue contacting surface, the biopolymer applicator configured for housing a biopolymer material at a location adjacent to the target tissue to receive the heat generated by the energy applied to the target tissue so as to allow the biopolymer material to change phase from a solid state to a molten state, and to allow the biopolymer to fill the dried tissue so as to reinforce the portions of the target tissue attached to one another and provide a hermetic seal once the biopolymer cools and returns to the solid state.

2. Apparatus in accordance with claim 1, wherein the energy applicator is a radio-frequency applicator.

3. Apparatus in accordance with claim 1, wherein the energy applicator is a ultrasonic applicator.

4. Apparatus in accordance with claim 1, wherein the energy applicator is a laser applicator.

5. Apparatus in accordance with claim 1, wherein the energy applicator is a microwave applicator.

6. Apparatus in accordance with claim 1, wherein the biopolymer applicator includes a porous plate.

7. Apparatus in accordance with claim 1, wherein the porous plate is thermally stable up to a temperature above 200° C.

8. Apparatus in accordance with claim 1, wherein the porous plate is a high temperature thermoplastic.

9. Apparatus in accordance with claim 8, wherein the high temperature thermoplastic is polytetrafluoroethylene (PTFE).

10. Apparatus in accordance with claim 1, wherein the porous plate is a porous ceramic.

11. Apparatus in accordance with claim 1, wherein the porous plate is a porous metal.

12. Apparatus in accordance with claim 11, wherein the porous plate is an electrode for the energy applicator using radio-frequency energy.

13. Apparatus in accordance with claim 6, wherein the porous plate includes a metal surface, and the porous plate is an electrode for the energy applicator using radio-frequency energy.

14. Apparatus in accordance with claim 6, wherein the biopolymer applicator includes the biopolymer material embedded within the porous plate.

15. Apparatus in accordance with claim 6, wherein the biopolymer applicator includes a reservoir adjacent to the biopolymer material embedded within the porous plate, and the reservoir containing an additional amount of the biopolymer material.

16. Apparatus in accordance with claim 15, wherein the reservoir includes a thermal regulator to control the change phase of the biopolymer material from the solid state to the molten state.

17. Apparatus in accordance with claim 16, wherein the thermal regulator includes a resistive element to directly heat the biopolymer material so as to control the change phase of the biopolymer material from the solid state to the molten state.

18. Apparatus in accordance with claim 16, wherein the thermal regulator includes at least one of a gas heat exchange system and a liquid heat exchange system to thermally regulate the biopolymer material so as to control the change phase of the biopolymer material from the solid state to the molten state.

19. Apparatus in accordance with claim 16, wherein the thermal regulator includes a thermoelectric cooling system to thermally regulate the biopolymer material so as to control the change phase of the biopolymer material from the solid state to the molten state.

20. Apparatus in accordance with claim 16, wherein the thermal regulator includes a direct cooling system to thermally regulate the biopolymer material so as to control the change phase of the biopolymer material from the solid state to the molten state.

21. Apparatus in accordance with claim 20, wherein the direct cooling system includes a saline infusion to thermally regulate the biopolymer material so as to control the change phase of the biopolymer material from the solid state to the molten state.

22. Apparatus in accordance with claim 15, wherein the reservoir includes a tube along a length of an endoscopic shaft in connection to the biopolymer applicator.

23. Apparatus in accordance with claim 15, wherein the reservoir is configured to actively pump the biopolymer material across the porous plate.

24. Apparatus in accordance with claim 15, further comprising biopolymer cartridges providing the biopolymer material, and wherein the reservoir is configured to receive the biopolymer cartridges to provide the biopolymer material to the biopolymer applicator.

25. Apparatus in accordance with claim 14, wherein the porous plate is configured to allow the biopolymer to passively wick into the target tissue.

26. Apparatus in accordance with claim 1, wherein the biopolymer material is electrically non-conductive.

27. Apparatus in accordance with claim 1, wherein the biopolymer material is polycaprolactone (PCL).

28. Apparatus in accordance with claim 1, wherein the biopolymer material is a polycaprolactone (PCL) copolymer.

29. Apparatus in accordance with claim 1, wherein the biopolymer material has a molecular weight less than 3000 MW, a melt temperature between about 37° C. and 200° C., and a melt viscosity less than about 1000 cps.

30. Apparatus in accordance with claim 1, wherein the biopolymer material has a glass transition temperature of about 60° C.

31. Apparatus in accordance with claim 1, wherein the biopolymer material has a bioabsorbable dye in order to provide visible feedback that the biopolymer material has been absorbed into the target tissue.

32. Apparatus in accordance with claim 31, wherein the bioabsorbable dye is methylene blue.

33. Apparatus in accordance with claim 1, wherein the first tissue contact surface and the second tissue contacting surface are adjacent to one another.

34. Apparatus in accordance with claim 1, wherein the first tissue contact surface and the second tissue contacting surface are remotely located from one another.

35. Apparatus in accordance with claim 1, wherein the first tissue contacting surface of the energy applicator is positioned on a set of jaws, and wherein the second tissue contacting surface of the biopolymer applicator is positioned on a set of jaws.

36. Apparatus in accordance with claim 35, wherein the first tissue contact surface and the second tissue contacting surface are adjacent to one another on one jaw of the set of jaws.

37. Apparatus in accordance with claim 35, wherein the first tissue contact surface and the second tissue contacting surface are remotely located from one another on opposed jaws of the set of jaws.

38. Apparatus in accordance with claim 35, wherein the biopolymer applicator includes a third tissue contacting surface, and wherein the second tissue contacting surface includes a first porous plate and the third tissue contacting surface includes a second porous plate.

39. Apparatus in accordance with claim 38, wherein the second tissue contacting surface and the third tissue contacting surface are remotely located from one another on opposed jaws of the set of jaws.

40. Apparatus in accordance with claim 35, further comprising a pressure controller in operable connection with the set of jaws, wherein the pressure controller has a low pressure setting and a high pressure setting, wherein the low pressure setting is configured to allow the jaws to apply a low amount of pressure so as to grasp and approximate tissue without excessive damage to the tissue, and wherein the high pressure setting is configured to allow the jaws to apply a high amount of pressure so as to clamp the tissue for welding with the energy applicator and the biopolymer applicator.

41. Apparatus in accordance with claim 40, wherein the pressure controller at the high pressure setting has an initial set-point during initial activation of the energy applicator, and the pressure controller has an escalating pressure up to a maximum set-point subsequent to initial activation of the energy applicator.

42. Apparatus in accordance with claim 35, further comprising a knife for division of the target tissue.

43. Apparatus in accordance with claim 42, further comprising at least one of the jaws forming a knife channel therein containing the knife, wherein the knife extends from the knife channel.

44. Apparatus in accordance with claim 42, wherein the knife is attached to a deployable electrode portion of a radio-frequency applicator of the energy applicator.

45. Apparatus in accordance with claim 35, wherein the energy applicator is a radio-frequency applicator, and electrodes are configured to cause current to flow in a lateral direction between the jaws.

46. Apparatus in accordance with claim 1, wherein the energy applicator and the biopolymer applicator are configured for lung resection.

47. Apparatus in accordance with claim 1, wherein the energy applicator and the biopolymer applicator are configured as a biopsy device to remove a tissue sample, and the biopolymer applicator is configured to reinforce the tissue sample with biopolymer.

48. Apparatus in accordance with claim 1, wherein the energy applicator and the biopolymer applicator are configured as a urinary incontinence treatment device.

49. Apparatus in accordance with claim 1, wherein the energy applicator and the biopolymer applicator are configured as a somnoplasty device.

50. Apparatus for reinforcement of tissue, the apparatus comprising:
an energy applicator positioned adjacent a first tissue contacting surface, the energy applicator configured to apply an amount of energy to generate heat within a target tissue so as to evaporate intracellular and extracellular water from the target tissue to create dried tissue; and
a biopolymer applicator disposed at a second tissue contacting surface, the biopolymer applicator configured for housing a biopolymer material at a location adjacent to the target tissue to receive the heat generated by the energy applied to the target tissue so as to allow the biopolymer material to change phase from a solid state to a molten state, and to allow the biopolymer to fill the dried tissue so as to provide a hemostatic barrier once the biopolymer cools and returns to the solid state.

51. A method of attaching and reinforcing tissue, the method comprising:
applying energy adjacent to tissue surfaces with an energy applicator, wherein the application of the energy is configured to generate an amount of heat within the tissue surfaces so as to evaporate intracellular and extracellular water from the target tissue to create dried tissue, and denature at least one of collagen and elastin within the tissue surfaces to attach portions of the tissue surfaces to one another; and
applying a biopolymer material into the tissue surfaces with a biopolymer applicator disposed on a housing in connection with the energy applicator, wherein the application of the biopolymer material includes housing the biopolymer material at a location adjacent to the tissue surfaces to receive the heat generated by the energy applied to the target tissue so as to allow the biopolymer material to change phase from a solid state to a molten state, and to allow the biopolymer to fill the dried tissue so as to reinforce the portions of the target tissue attached to one another and provide a hermetic seal once the biopolymer cools and returns to the solid state.

52. A method of reinforcing tissue, the method comprising:
applying energy adjacent a tissue surface with an energy applicator, wherein the application of the energy is configured to generate an amount of heat within a target tissue so as to evaporate intracellular and extracellular water from the target tissue to create dried tissue; and
applying a biopolymer material into the target tissue with a biopolymer applicator disposed on a housing in connection with the energy applicator, wherein the application of the biopolymer includes housing the biopolymer material at a location adjacent to the target tissue to receive the heat generated by the energy applied to the target tissue so as to allow the biopolymer material to change phase from a solid state to a molten state, and to allow the biopolymer to fill the dried tissue so as to provide a hemostatic barrier once the biopolymer cools and returns to the solid state.

* * * * *